United States Patent
Tsujimoto et al.

(10) Patent No.: US 8,947,519 B2
(45) Date of Patent: Feb. 3, 2015

(54) IMAGE PROCESSING APPARATUS, IMAGE PROCESSING SYSTEM, IMAGE PROCESSING METHOD, AND IMAGE PROCESSING PROGRAM

(71) Applicant: Canon Kabushiki Kaisha, Tokyo (JP)

(72) Inventors: Takuya Tsujimoto, Kawasaki (JP); Kazuyuki Sato, Yokohama (JP); Toru Sasaki, Yokohama (JP); Hidetoshi Tsuzuki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/910,420

(22) Filed: Jun. 5, 2013

(65) Prior Publication Data

US 2014/0015954 A1  Jan. 16, 2014

Related U.S. Application Data

(63) Continuation of application No. PCT/JP2012/083818, filed on Dec. 27, 2012.

(30) Foreign Application Priority Data

Dec. 27, 2011 (JP) ................. 2011-286783
Dec. 26, 2012 (JP) ................. 2012-282784

(51) Int. Cl.
*H04N 7/18* (2006.01)
*G02B 21/36* (2006.01)
*G06T 3/40* (2006.01)
*G06F 19/00* (2011.01)

(52) U.S. Cl.
CPC .............. *G02B 21/365* (2013.01); *G02B 21/36* (2013.01); *G06T 3/40* (2013.01); *G06F 19/321* (2013.01); *G06F 19/366* (2013.01)
USPC .............................................. 348/79; 348/80

(58) Field of Classification Search
CPC .... H01J 37/28; H01J 37/224; G01N 21/6458; G02B 21/24
USPC ....................................... 348/79–80
See application file for complete search history.

(56) References Cited

U.S. PATENT DOCUMENTS 8,605,144 B2 * 12/2013 Takayama ........................ 348/79
2012/0127297 A1 * 5/2012 Baxi et al. ........................ 348/79
2012/0236137 A1 * 9/2012 Kawashima .................... 348/79

FOREIGN PATENT DOCUMENTS

JP   2002251464 A   9/2002
JP   2005321657 A   11/2005
JP   2008096582 A   4/2008

* cited by examiner

*Primary Examiner* — Andy Rao
(74) *Attorney, Agent, or Firm* — Canon USA Inc. IP Division

(57) ABSTRACT

An image processing apparatus which processes virtual slide image data to be displayed in an image display apparatus includes an image data obtaining unit which obtains image data obtained by capturing an image of a target object, and an image data generation unit which generates display image data corresponding to the image of the target object to be displayed in the image display apparatus in a display magnification corresponding to a predetermined field number of a microscope.

19 Claims, 10 Drawing Sheets

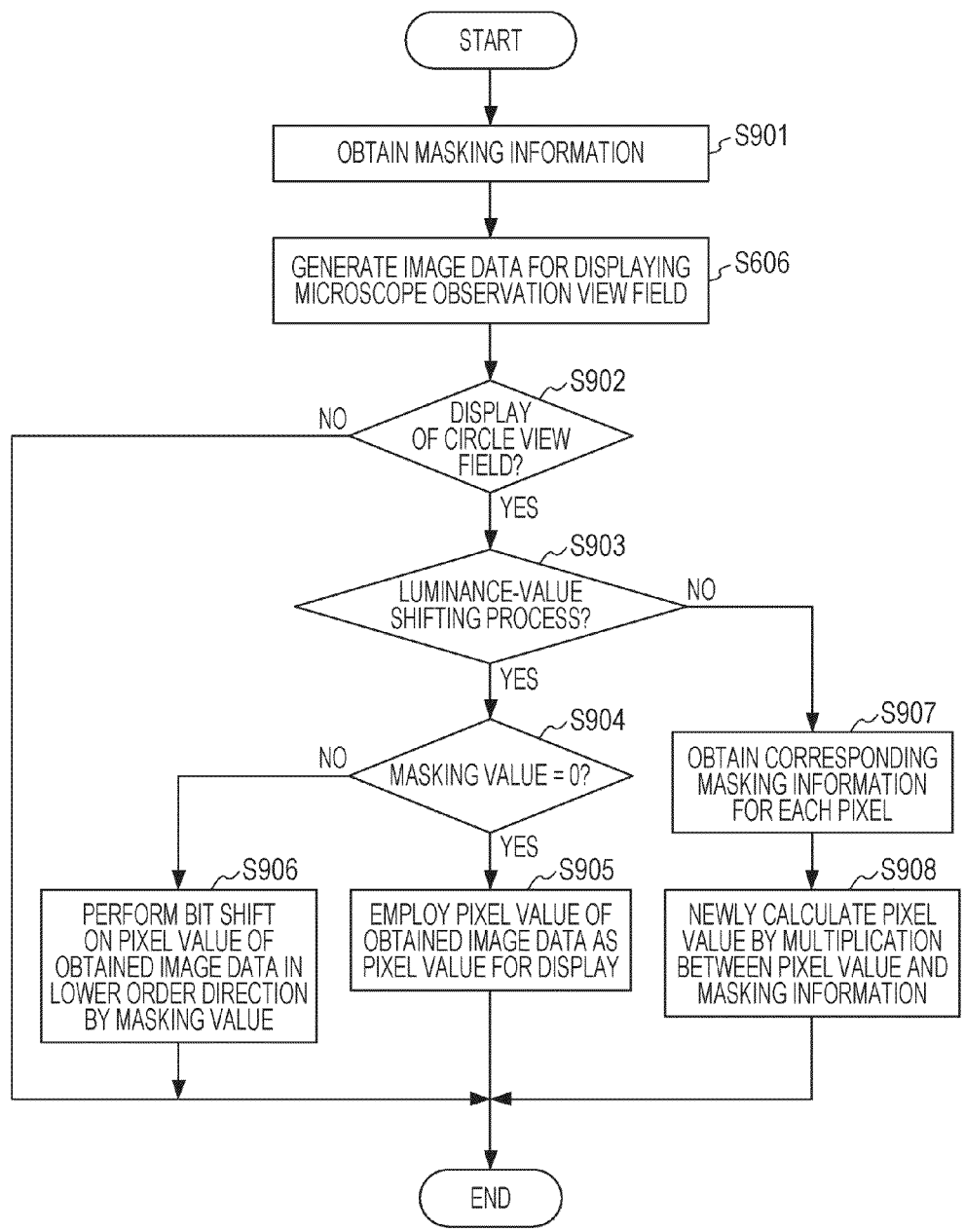

ion No. PCT/JP2012/083818, filed Dec. 27, 2012, which claims the benefit of Japanese Patent Application No. 2011-286783, filed Dec. 27, 2011 and Japanese Patent Application No. 2012-282784, filed Dec. 26, 2012, all of which are hereby incorporated by reference herein in their entirety.

IMAGE PROCESSING APPARATUS, IMAGE PROCESSING SYSTEM, IMAGE PROCESSING METHOD, AND IMAGE PROCESSING PROGRAM

CROSS-REFERENCE TO RELATED APPLICATIONS

This application is a Continuation of International Patent Application No. PCT/JP2012/083818, filed Dec. 27, 2012, which claims the benefit of Japanese Patent Application No. 2011-286783, filed Dec. 27, 2011 and Japanese Patent Application No. 2012-282784, filed Dec. 26, 2012, all of which are hereby incorporated by reference herein in their entirety.

TECHNICAL FIELD

The present invention relates to an image processing apparatus, an image processing method, an image processing system, and a program.

BACKGROUND ART

In recent years, in a field of pathology, a virtual slide system which enables pathological diagnosis on a display by capturing an image of a test sample (a specimen) placed on a prepared slide and digitalizing the image has received attention instead of optical microscopes which are tools of pathological diagnosis. Since pathological diagnosis images are digitalized using the virtual slide system, images of test samples which have been conventionally obtained by optical microscopes may be used as digital data. As a result, it is expected that speedy remote diagnosis, explanation for patients using digital images, sharing of rare cases, and efficient education and practical training are realized.

In order to realize an operation equivalent to operations of optical microscopes using a virtual slide system, an entire test sample placed on a prepared slide is preferably digitalized. By digitalizing the entire test sample, digital data generated by the virtual slide system may be observed through viewer software which operates in PCs (Personal Computers) and work stations. The number of pixels obtained when the entire test sample is digitalized is from several hundred millions to several billions in general, that is, a considerably large amount of data.

Although the amount of data generated by the virtual slide system is large, various types of observation from observation of a micro image (a detail expansion image) to observation of a macro image (an overview image) may be performed by performing a scaling process using a viewer. Accordingly, improved usability is realized. By obtaining all information to be used in advance, images having resolutions and magnifications desired by a user including an image having a low magnification and an image having a high magnification may be immediately displayed.

As a related art, a medical image display apparatus for supporting diagnoses made by doctors by displaying medical image data in a real size in a display unit (a display screen) in accordance with a pixel pitch of the medical image data and a pixel pitch of the display unit of an image display apparatus has been proposed.

CITATION LIST

Patent Literature

PTL 1 Japanese Patent Laid-Open No. 2002-251464
A virtual slide image is displayed after image data obtained by capturing an image of an observation object is subjected to image processing, and therefore, the virtual slide image is different from an image observed by a microscope in terms of a size of a view field. In general, for users who observe images of objects (specimens) using optical microscopes, it is difficult to efficiently perform diagnosis using a virtual slide since an observation view-field region of an optical microscope image and that of a virtual slide image are different from each other.

Accordingly, an object of the present invention is to propose an image processing apparatus capable of generating a virtual slide image having an observation view field equivalent to an observation view field of an optical microscope image.

SUMMARY OF INVENTION

The present invention provides an image processing apparatus which processes virtual slide image data to be displayed in an image display apparatus. The image processing apparatus includes an image data obtaining unit configured to obtain image data obtained by capturing an image of a target object, and an image data generation unit configured to generate display image data corresponding to the image of the target object to be displayed in the image display apparatus in a display magnification corresponding to a predetermined field number of a microscope.

The present invention further provides an image processing method for processing a virtual slide image. The image processing method includes an image data obtaining step of obtaining image data obtained by capturing an image of a target object, and an image data generation step of generating display image data representing an image to be displayed in the image display apparatus in a display magnification corresponding to a predetermined field number of a microscope.

The present invention further provides an image processing system which includes the image processing apparatus described above, and an image display apparatus which displays a virtual slide image processed by the image processing apparatus in a display magnification corresponding to a predetermined field number of a microscope.

The present invention further includes a program which causes a computer to execute the steps of the image processing method described above.

Further features of the present invention will become apparent from the following description of exemplary embodiments with reference to the accompanying drawings.

BRIEF DESCRIPTION OF DRAWINGS

FIG. 9 is a flowchart illustrating a flow of a process of generating image data for displaying microscope observation view field performed by the image processing apparatus according to the present invention in detail.

DESCRIPTION OF EMBODIMENTS

Figure 1:
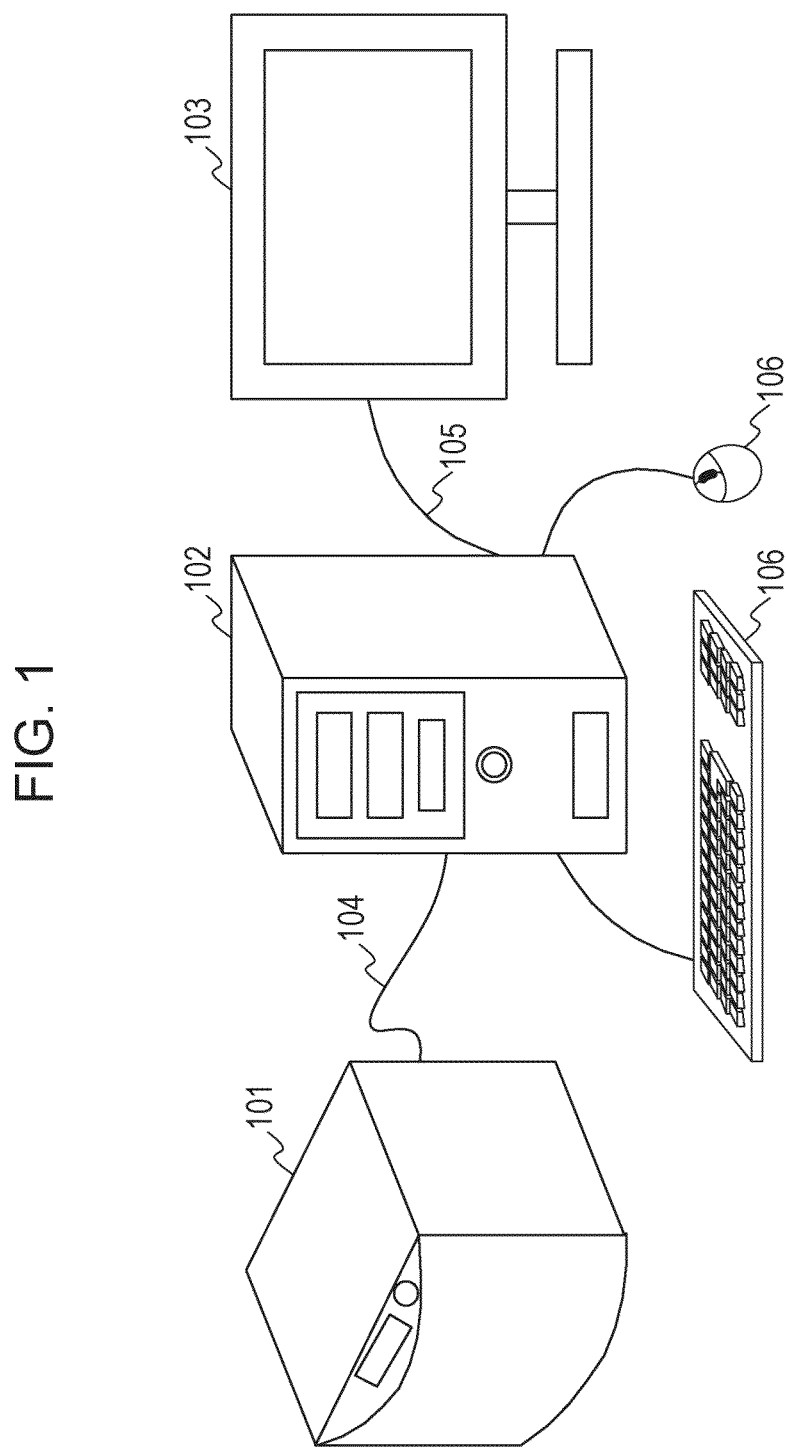
FIG. 1 is an overall view schematically illustrating a configuration of apparatuses included in an image processing system employing an image processing apparatus according to the present invention.

Hereinafter, embodiments of the present invention will be described with reference to the accompanying drawings.

An image processing apparatus according to preferred embodiments of the present invention processes virtual-slide image data to be displayed in an image display apparatus and at least includes an image data obtaining unit and an image data generation unit. The image data generation unit preferably generates image data for display corresponding to an image of a target object to be displayed in the image display apparatus in a display magnification corresponding to a predetermined field number of a microscope.

A predetermined microscope view field is preferably determined in accordance with information stored in advance in the image processing apparatus or an external storage apparatus or determined in accordance with a user's instruction. A type of view field to be reproduced is preferably stored in advance as the information described above. The information stored in advance preferably includes at least one of initial view field information (information selected as a microscope view field when the user does not issue an instruction, which is hereinafter simply referred to as "initial information") and a plurality of specific view field information items of an existing microscope (a plurality of microscope view field information items selectable by the user). Note that the initial view field information may be stored by selecting one of the plurality of microscope view field information items. Note that the microscope view field information includes at least one of a field number and a magnification of an objective lens. Furthermore, an observation region newly determined in accordance with a user's instruction may be stored as additional view field information which may be selected as an option of the view field information. Moreover, observation regions newly determined in accordance with user's instructions may be managed for individual users.

The image data generation unit may determine the display magnification such that a diameter of a predetermined actual view field of a microscope coincides with a length of a long side or a length of a short side of a display screen of the image display apparatus. Furthermore, the image data generation unit may determine the display magnification in accordance with information on a view field of an existing microscope. Furthermore, the image data generation unit may determine the display magnification using a predetermined one of a plurality of information items on a view field of an existing microscope. Moreover, the image data generation unit may determine the display magnification using one of a plurality of information items on a view field of an existing microscope selected by a user. Furthermore, the image data generation unit may generate image data for display in accordance with the number of pixels of the image display apparatus. Furthermore, the image data generation unit may generate image data for display in accordance with a magnification of an objective lens obtained when the target object is captured. Note that the term "image data for display" is referred to as "display image data" where appropriate in the following description and the accompanying drawings.

The image data generation unit preferably generates image data for display in which a display magnification thereof is changed by a pixel magnification represented by an equation below. When the image data for display is generated by the pixel magnification below, a microscope view field and an image generated by the image processing apparatus may coincide with each other.

Pixel Magnification=((the Number of Pixels of Long Side or Short Side of Display Screen of Image Display Apparatus)/((Predetermined Field Number of Microscope)/(Pixel Pitch of Image-Pickup Sensor)))×((Display Magnification in Display Screen of Image Display Apparatus)/(Magnification of Objective Lens in Image Capturing))

Here, in this specification and the present invention, a proportion of information for one pixel of the image-pickup sensor to pixels in the display screen of the image display apparatus is defined as a pixel magnification. In general, display in which one pixel of image data corresponds to one pixel of a display screen of an image display apparatus is referred to as pixel actual-size display. In this specification and the present invention, it is assumed that information obtained from one pixel of the image-pickup sensor corresponds to one pixel of image data. In this case, a pixel magnification of pixel actual-size display is 1.

Note that, when a pixel pitch of a long side is different from that of a short side, a pixel magnification is defined using "Pixel Pitch of Image-Pickup Sensor" and a pixel pitch of a side selected in "the Number of Pixels of Long Side or Short Side of Display Screen of Image Display Apparatus". Note that, although the terms "long side" and "short side" are used assuming a display screen of a rectangular shape, when a display screen has an oval shape, a long axis is defined as a long side and a short axis is defined as a short side.

Furthermore, when image data for display is generated by a pixel magnification below, sizes of images actually displayed in image display apparatuses having display screens of different sizes may coincide with each other.

Pixel Magnification=(Enlargement Magnification)×(Pixel Pitch of Image-Pickup Sensor)/(Pixel Pitch in Display Screen of Image Display Apparatus)

Here, the enlargement magnification represents a degree of enlargement of the target image displayed in the display screen. The relationship between the enlargement magnification and the display magnification is represented by an equation below in accordance with the equation above and the following equation:

Pixel Magnification=(Display Magnification)/(Magnification of Objective Lens in Image Capturing).

Enlargement Magnification=(Display Magnification)×(Pixel Pitch in Display Screen of Image Display Apparatus)/((Pixel Pitch of Image-Pickup Sensor)×(Magnification of Objective Lens in Image Capturing))

The image processing apparatus may further include a mode selection unit. The mode selection unit preferably selects at least one of the following three modes (1) to (3) for selecting an image to be displayed in the image display apparatus:
(1) a mode for displaying display image data generated in a pixel magnification represented by the following equation:

> Pixel Magnification=((the Number of Pixels of Long Side or Short Side of Display Screen of Image Display Apparatus)/((Predetermined Field Number of Microscope)/(Pixel Pitch of Image-Pickup Sensor)))×((Display Magnification in Display Screen of Image Display Apparatus)/(Magnification of Objective Lens in Image Capturing)).

(2) a mode for displaying display image data as pixel actual-size display, and
(3) a mode for displaying display image data generated in a pixel magnification represented by the following equation:

> Pixel Magnification=(Enlargement Magnification)×(Pixel Pitch of Image-Pickup Sensor)/(Pixel Pitch in Display Screen of Image Display Apparatus).

Note that the enlargement magnification is obtained by the following calculation:

> (Display Magnification)×(Pixel Pitch in Display Screen of Image Display Apparatus)/((Pixel Pitch of Image-Pickup Sensor)×(Magnification of Objective Lens in Image Capturing)).

Note that the mode (1) corresponds to a mode for reproducing a microscope view field.

An image processing method according to a preferred embodiment of the present invention processes virtual-slide image data and at least includes an image data obtaining step and an image data generation step. In the image data obtaining step, image data is obtained by capturing an image of a target object is obtained. In the image data generation step, display image data for displaying an image in a display magnification corresponding to the field number of the microscope is generated so that an (observation view field) image similar to an image viewed by the microscope is formed.

In the image data generation step, image data for display in which a display magnification thereof is changed by a pixel magnification represented by the following equation is preferably generated.

> Pixel Magnification=((the Number of Pixels of Long Side or Short Side of Display Screen of Image Display Apparatus)/((Predetermined Field Number of Microscope)/(Pixel Pitch of Image-Pickup Sensor)))×((Display Magnification in Display Screen of Image Display Apparatus)/(Magnification of Objective Lens in Image Capturing)).

A program according to the present invention causes a computer to execute the steps of the image processing method described above.

An image processing system according to the present invention includes an image processing apparatus which processes a virtual slide image and an image display apparatus which displays a virtual slide image processed by the image processing apparatus. Moreover, the image processing system may further include a display unit which displays image data generated by the image data generation unit in the image display apparatus. The image data obtaining unit obtains image data obtained by capturing an image of a target object. The image data generation unit generates display image data for displaying a virtual slide image processed by the image processing apparatus in the image display apparatus in a display magnification corresponding to the field number of the microscope. Note that the term "image display apparatus" is simply referred to as "display apparatus" where appropriate in the following description and the accompanying drawings.

The embodiments of the image processing apparatus may be reflected to an image processing method, a program, and an image processing system of the present invention.

Hereinafter, embodiments of the present invention will be described.

First Embodiment

An image processing apparatus according to the present invention may be used in an image processing system including an image-pickup apparatus and an image display apparatus. The image processing system will be described with reference to FIG. 1.

Configuration of Apparatuses Included in Image Processing System

FIG. 1 is an overall view schematically illustrating the image processing system employing the image processing apparatus according to the present invention. The system includes an image-pickup apparatus (a microscope apparatus or a virtual slide apparatus) 101, an image processing apparatus 102, and an image display apparatus 103. The system also includes a function of obtaining a 2D image of a test sample (a specimen) of a target of image capturing and displaying the 2D image. In this embodiment, the image-pickup apparatus 101 and the image processing apparatus 102 are connected to each other through a dedicated or general-purpose I/F cable 104, and the image processing apparatus 102 and the image display apparatus 103 are connected to each other through a general-purpose I/F cable 105.

As the image-pickup apparatus 101, a virtual slide apparatus which captures a single 2D image or a plurality of 2D images in different positions in a 2D plane direction and which has a function of outputting digital images may be suitably used. To obtain a 2D image, a solid-state image-pickup element such as a CCD (Charge Coupled Device) or a CMOS (Complementary Metal Oxide Semiconductor) is suitably used. Instead of the virtual slide apparatus, a digital microscope apparatus constituted by attaching a digital still camera to an eye piece of a general optical microscope may be used as the image-pickup apparatus 101. Note that even when an image is captured using a digital still camera, the captured image may be divided into an observation region and an out-of-observation region in a case where high-magnification display is selected or a case where image data for display is formed by synthesizing original image data items obtained by performing image capturing a number of times on different image-pickup regions.

As the image processing apparatus 102, an apparatus which has a function of generating data to be displayed in the image display apparatus 103 from single original image data or a plurality of original image data items obtained from the image-pickup apparatus 101 in response to a request from a user may be suitably used. As the image processing apparatus 102, an apparatus such as a general computer or a work station which includes hardware resources such as a CPU (a central processing unit), a RAM, a storage device, and various I/Fs including an operation unit may be used. As the storage device, a mass-storage device such as a hard disk drive may be suitably used. The storage device preferably stores programs and data which realize various processes which will be described below and an OS (Operating System). The functions described above are realized by executing the programs after the CPU loads the programs and the data to be used from the storage device to the RAM. An operation unit 106 includes a keyboard and a mouse and is used by the user to input various instructions. The operation unit 106 may be a component included in the image processing apparatus 102.

The image display apparatus 103 of this embodiment is a display such as a CRT or a liquid crystal display which displays an observation image obtained as a result of a calculation process performed by the image processing apparatus 102. Note that a printing apparatus which prints and displays an image may be used as the image display apparatus. Hereinafter, the image display apparatus is referred to as a "display" where appropriate.

In the example of FIG. 1, the image-pickup system includes three apparatuses, i.e., the image-pickup apparatus 101, the image processing apparatus 102, and the image display apparatus 103. However, a configuration of the present invention is not limited to this configuration. For example, the image processing apparatus 102 integrated with the image display apparatus 103 may be used or the function of the image processing apparatus 102 may be incorporated in the image-pickup apparatus 101. Alternatively, the functions of the image-pickup apparatus 101, the image processing apparatus 102, and the image display apparatus 103 may be realized by a single apparatus. Conversely, the function of each apparatus such as the image processing apparatus 102 may be divided and realized by a plurality of apparatuses.

Functional Configuration of Image-Pickup Apparatus

Figure 2:
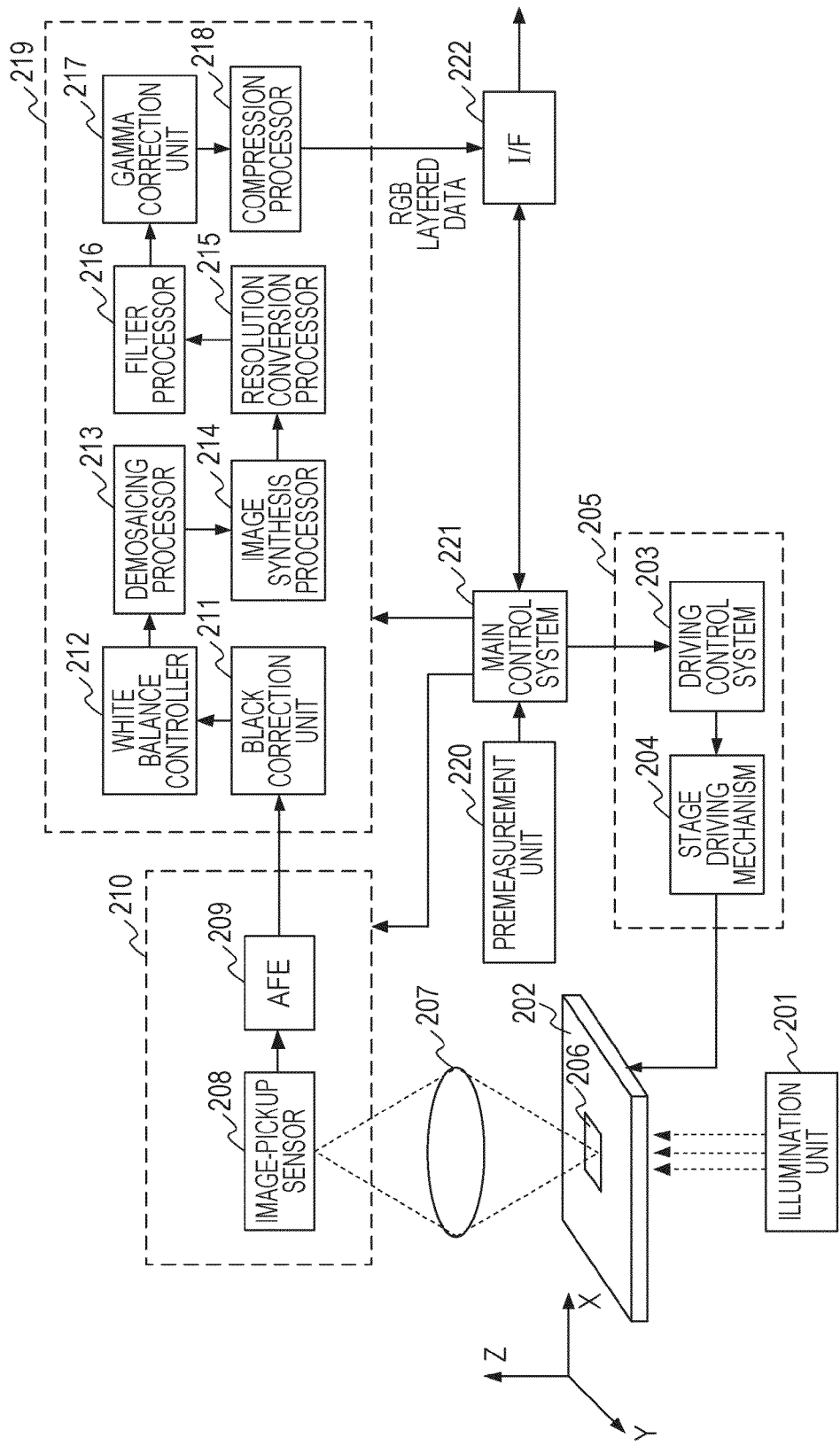
FIG. 2 is a functional block diagram illustrating a functional configuration of an image-pickup apparatus included in the image processing system employing the image processing apparatus according to the present invention.

FIG. 2 is a functional block diagram illustrating a functional configuration of the image-pickup apparatus 101.

The image-pickup apparatus 101 of this embodiment briefly includes an illumination unit 201, a stage 202, a stage control unit 205, an image-forming optical system 207, an image-pickup unit 210, a development processing unit 219, a premeasurement unit 220, a main control system 221, and a data output unit (I/F) 222.

The illumination unit 201 of this embodiment uniformly illuminates a prepared slide 206 placed on the stage 202, and is preferably includes a light source, an illumination optical system, and a control system for driving the light source. The stage 202 of this embodiment is controlled to be driven by the stage control unit 205 so as to be moved in three axes directions, i.e., X, Y, and Z directions. The prepared slide 206 is obtained by attaching a piece of tissue or smear tissue serving as an observation target on a slide glass and fixing the piece of tissue or the smear tissue under a cover glass with a mounting agent.

The stage control unit 205 of this embodiment includes a driving control system 203 and a stage driving mechanism 204. In this embodiment, the driving control system 203 receives an instruction issued by the main control system 221 so as to perform driving control on the stage 202. A direction and an amount of movement of the stage 202 are determined in accordance with positional information and thickness information (distance information) of a specimen measured by the premeasurement unit 220 and an instruction input by the user where appropriate in this embodiment. The stage driving mechanism 204 of this embodiment drives the stage 202 in accordance with an instruction issued by the driving control system 203.

The image-forming optical system 207 of this embodiment is a lens group used to form an optical image of the specimen placed on the prepared slide 206 in an image-pickup sensor 208.

The image-pickup unit 210 of this embodiment includes the image-pickup sensor 208 and an analog front end (AFE) 209. The image-pickup sensor 208 of this embodiment is a 1D image sensor or a 2D image sensor which converts a 2D optical image into electric physical quantity by photoelectric conversion. As the image-pickup sensor 208, a CCD device or a CMOS device is used, for example. When a 1D sensor is used, a 2D image may be obtained when the 1D sensor performs scanning in a scanning direction. The image-pickup sensor 208 of this embodiment outputs an electric signal having a voltage value corresponding to light intensity. When a color image is to be obtained as a captured image, an image sensor of a single panel to which color filters of a Bayer array are attached may be used as the image-pickup sensor 208, for example. The image-pickup unit 210 of this embodiment may capture divided images of the specimen by performing the image capturing while the stage 202 is moved in the X and Y directions.

The AFE 209 of this embodiment is a circuit which converts an analog signal output from the image-pickup sensor 208 into a digital signal. The AFE 209 preferably includes an H/V driver, a CDS (Correlated double sampling) circuit, an amplifier, an AD converter, and a timing generator, which will be described hereinafter. The H/V driver of this embodiment converts a vertical synchronization signal and a horizontal synchronization signal used to drive the image-pickup sensor 208 into potentials suitable for driving of the sensor. The CDS of this embodiment is a correlated double sampling circuit which removes noise of a fixed pattern. The amplifier is an analog amplifier which controls a gain of an analog signal from which noise is removed by the CDS. The AD converter of this embodiment converts an analog signal into a digital signal. When data of eight bits is output in the last stage of the image-pickup apparatus, the AD converter preferably converts an analog signal into a digital signal which is quantized in a range from approximately 10 bits to approximately 16 bits and preferably outputs the digital signal taking a process in a later stage into consideration. Here, the converted sensor output data is referred to as RAW data. In this embodiment, the RAW data is subjected to a development process performed by the development processing unit 219 in the later stage. The timing generator of this embodiment generates a signal used to control a timing of the image-pickup sensor 208 and a timing of the development processing unit 219 in the later stage.

When a CCD sensor is used as the image-pickup sensor 208, the AFE 209 is normally used as an essential component. On the other hand, when a CMOS image sensor capable of performing digital output is used as the image-pickup sensor 208, a function of the AFE 209 is normally incorporated in the sensor. Furthermore, although not shown, in this embodiment, an image-pickup controller which controls the image-pickup sensor 208 is provided so as to perform control of an operation of the image-pickup sensor 208, control of operation timings of a shutter speed, a frame rate, and control of an ROI (Region Of Interest).

The development processing unit 219 of this embodiment includes a black correction unit 211, a white balance controller 212, a demosaicing processor 213, an image synthesis processor 214, a resolution conversion processor 215, a filter processor 216, a gamma correction unit 217, and a compression processor 218. The black correction unit 211 of this embodiment performs a process of subtracting black correction data obtained when light is blocked from pixels of the RAW data. The white balance controller 212 of this embodiment performs a process of reproducing a preferable white color by controlling gains of colors of R, G, and B in accordance with color temperature of light of the illumination unit 201. Specifically, white balance correction data is added to the RAW data which has been subjected to black correction. In a case of a monochrome image, the white balance control process is not performed. The development processing unit 219 of this embodiment generates layered image data which will be described hereinafter from divided image data items of the specimen obtained by the image-pickup unit 210.

The demosaicing processor 213 of this embodiment performs a process of generating image data items of the colors of R, G, and B from the RAW data of the Bayer array. The demosaicing processor 213 of this embodiment calculates values of the colors of R, G, and B of a target pixel by performing interpolation using values of peripheral pixels (including pixels of the same color and pixels of the other colors). Furthermore, the demosaicing processor 213 further performs a process of correcting a defect pixel (an interpolation process). Note that, when the image-pickup sensor 208 does not include color filters and a monochrome image is obtained, the demosaicing process is not performed.

The image synthesis processor 214 of this embodiment performs a process of generating image data of a large volume within a desired image-pickup range by connecting image data items obtained by dividing the image-pickup range and capturing images of the divided image-pickup ranges using the image-pickup sensor 208. In general, since a range of the specimen is larger than the image-pickup range obtained by one image capturing operation performed by a general image sensor, single 2D image data is generated by connecting divided image data items. Assuming that an image in a range of 10 mm square on the prepared slide 206 is captured in resolution capability of 0.25 µm, the number of pixels on one side is 40 thousands (10 mm/0.25 µm) and the total number of pixels is the square of 40 thousands, that is, 1.6 billions. When image data having pixels of 1.6 billions is to be obtained by the image-pickup sensor 208 having pixels of 10 M (10 millions), image capturing is performed after a region is divided into 160 regions (1.6 billions/10 millions). Note that examples of a method for connecting a plurality of image data items include a method for connecting image data items by performing positioning in accordance with positional information of the stage 202, a method for connecting image data items by associating corresponding points or corresponding lines in a plurality of divided images with one another, and a method for connecting image data items in accordance with positional information items of the divided image data items. The image data may be smoothly connected by means of an interpolation process such as zero-order interpolation, linear interpolation, or higher-order interpolation. Although generation of a single image of a large volume is considered in this embodiment, divided images may be connected to one another when data for display is generated as a function of the image processing apparatus 102. Note that the term "data for display" is simply referred to as "display data" where appropriate in the following description and the accompanying drawings.

The resolution conversion processor 215 of this embodiment performs a process of generating an image of a magnification corresponding to a display magnification in advance through resolution conversion so that a 2D image of a large volume generated by the image synthesis processor 214 is displayed at high speed. The resolution conversion processor 215 generates image data items in a plurality of levels from a low magnification to a high magnification and configures the image data items as image data having a collective layer configuration. The image data obtained by the image-pickup apparatus 101 is preferably captured image data of a high resolution and a high resolving power in terms of diagnosis. However, as described above, in a case where a size-reduced image corresponding to image data having billions of pixels is to be displayed, if resolution conversion is performed every time a display request is issued, a speed of a process may be lowered. Therefore, it is preferable that layered images of different layers which have different magnifications are provided in advance, image data of a magnification similar to a display magnification is selected from the provided layered images in response to a request for display, and the magnification is controlled in accordance with the display magnification. Taking image quality into consideration, display data is more preferably generated from image data of a high magnification. When an image is captured in a high resolution, layered image data for display is generated by reducing a size of image data having the highest resolving power by a resolution conversion method. Examples of the resolution conversion method include bilinear which is a 2D linear interpolation process and bicubic employing a 3D interpolation function.

The filter processor 216 of this embodiment is a digital filter which realizes suppression of high-frequency components included in an image, noise removal, and resolution feeling emphasis. The gamma correction unit 217 of this embodiment executes a process of adding inverse characteristics to an image in accordance with gradation expression characteristics of general display devices and executes gradation conversion in accordance with a visual feature of human beings by performing gradation compression of a high luminance section or a dark section process. In this embodiment, since an image is obtained for the purpose of observation of a configuration, the gradation conversion suitable for a display process performed in a later stage is performed on image data.

The compression processor 218 of this embodiment performs an encoding process for compression in order to attain high efficiency of transmission of 2D image data of a large volume and reduce the volume of the 2D image data to be stored. As a method for compressing a still image, a standardized encoding method such as JPEG (Joint Photographic Experts Group), or JPEG 2000 or JPEG XR which is improved and advanced JPEG may be used.

The premeasurement unit 220 of this embodiment measures positional information of the specimen on the prepared slide 206, information on a distance to a desired focal position, and a parameter used for controlling light intensity in accordance with a thickness of the specimen in advance. Since the premeasurement unit 220 obtains the information before main measurement (obtainment of captured image data), efficient image capturing may be performed. When positional information in a 2D plane is to be obtained, a 2D image-pickup sensor having a resolving power lower than that of the image-pickup sensor 208 may be used. The premeasurement unit 220 of this embodiment recognizes a position of the specimen in an XY plane from an obtained image. When the distance information and the thickness information are to be obtained, a laser displacement meter or shack-Hartmann measurement equipment may be used.

The main control system 221 of this embodiment controls the various units described hereinabove. The main control system 221 and the development processing unit 219 may be controlled by a control circuit including a CPU, a ROM, and a RAM. For example, programs and data are stored in the ROM in advance and the CPU executes the programs using the RAM as a work memory so that functions of the main control system 221 and the development processing unit 219 are realized. Examples of the ROM include devices such as an EEPROM and a flash memory. Examples of the RAM include a DDR3 DRAM device. Note that the function of the development processing unit 219 may be replaced by a dedicated hardware device configured as an ASIC.

The data output unit 222 of this embodiment is an interface used to transmit an image of colors of R, G, and B generated by the development processing unit 219 to the image processing apparatus 102. The image-pickup apparatus 101 and the image processing apparatus 102 of this embodiment are connected to each other by an optical communication cable.

Instead of the cable, a general-purpose interface of a USB or a Gigabit Ethernet (registered trademark) may be used.

Functional Configuration of Image Processing Apparatus

Figure 3:
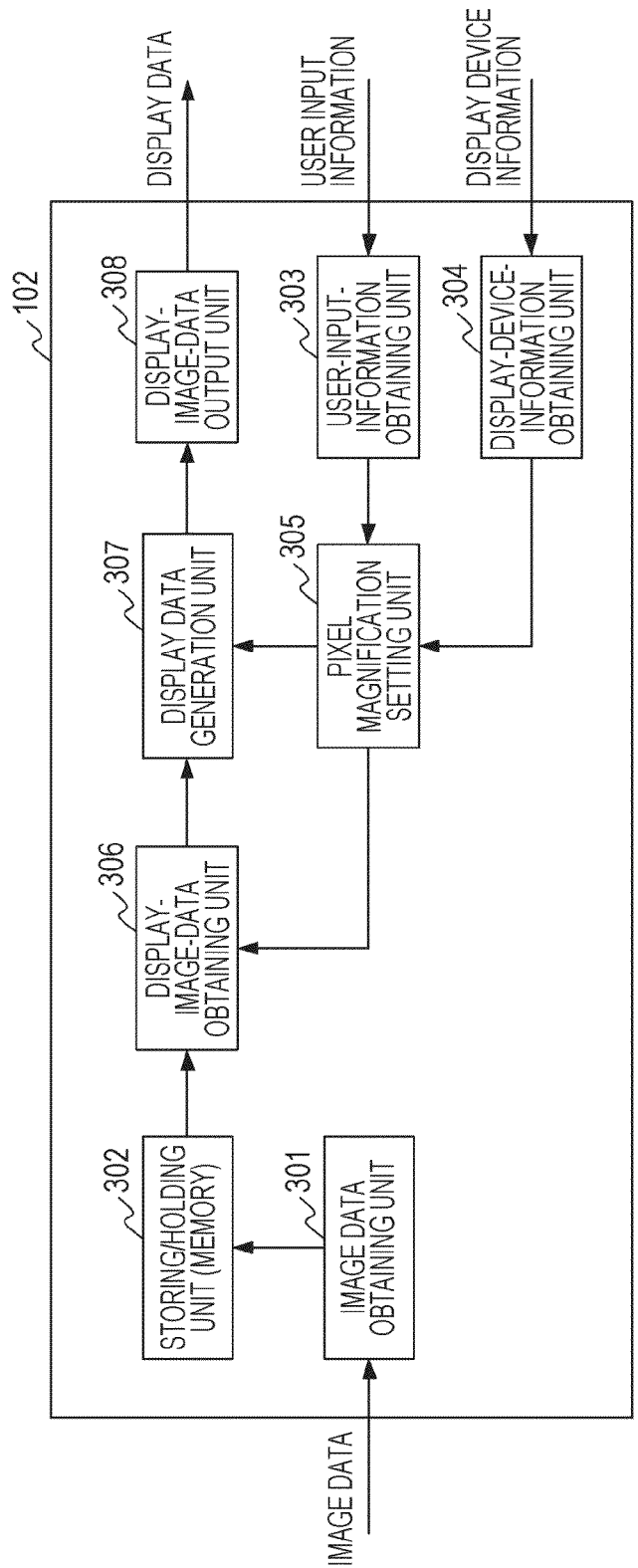
FIG. 3 is a functional block diagram illustrating a configuration of the image processing apparatus according to the present invention.

FIG. 3 is a block diagram illustrating a functional configuration of the image processing apparatus 102 according to the present invention.

The image processing apparatus 102 briefly includes an image data obtaining unit 301, a storing/holding unit (memory) 302, a user-input-information obtaining unit 303, a display-device-information obtaining unit 304, a pixel magnification setting unit 305, a display-image-data obtaining unit 306, a display data generation unit 307, and a display-image-data output unit 308.

The image data obtaining unit 301 of this embodiment obtains image data captured by the image-pickup apparatus 101. The image data of this embodiment at least corresponds to divided data items of an image of colors of R, G, and B obtained by capturing an image of the specimen in a divided manner, single 2D image data obtained by synthesizing the divided image data items, or image data items which are layered for individual display magnifications on the basis of the 2D image data. Note that the divided image data items may be monochrome image data items. Note that a pixel pitch of the image-pickup sensor 208 of the image-pickup apparatus 101 and magnification information of the objective lens which are included in image-pickup specification are added to the image data.

The storing/holding unit 302 of this embodiment obtains, stores, and holds image data supplied from an external apparatus through the image data obtaining unit 301. Furthermore, the storing/holding unit 302 preferably stores a plurality of view field information items of the practically-existing microscope described above and information on a selected one of the view field information items to be used as initial information.

The user-input-information obtaining unit 303 of this embodiment obtains information input by the user such as an instruction for updating data for displaying an image including change of a display position and scaling, selection of a display mode, or specifying of an observation region (for example, selection of one of the plurality of magnification view field information items held by the storing/holding unit 302) through the operation unit 106 such as the mouse or the keyboard. The display mode of this embodiment includes a mode for reproducing a microscope observation view field and a mode for not reproducing a microscope observation view field. The specifying of a display mode may be the same as specifying of a display magnification. Furthermore, in addition to the specifying of a display mode, a setting of a field number of the microscope which serves as a reproduction source used for reproduction of the microscope observation view field may be performed. Note that, in general, a field number is in a range from approximately 18 mm to approximately 26.5 mm.

The display-device-information obtaining unit 304 of this embodiment obtains display area information (a screen resolution and a display size) of the display and information on a display magnification of an image currently displayed which are stored in the image display apparatus 103.

The pixel magnification setting unit 305 of this embodiment generates control data used to set a display magnification in accordance with a user's instruction obtained by the user-input-information obtaining unit 303. Furthermore, the pixel magnification setting unit 305 calculates a size of image data for display in accordance with the set pixel magnification and notifies the display-image-data obtaining unit 306 of the image-data size.

At least one of the control data and the display-image-data size output from the pixel magnification setting unit 305 is affected by the initial view field information or the observation region information described above which is specified by the user. Here, examples of the observation region information specified by the user include one of the practically-existing microscope view field information items selected by the user, information which is obtained by partially modifying such an existing microscope view field information item and which is specified by the user, and information on an observation region specified by the user irrespective of the magnification view field information. The initial view field information may be read from the storing/holding unit 302. In addition, at least one of the control data and the display-image-data size output from the pixel magnification setting unit 305 of this embodiment is preferably affected by information on the image display apparatus 103 including a magnification of the objective lens at a time of image capturing, information on a pixel pitch of the image-pickup sensor 208 at a time of image capturing, a pixel pitch of a display screen of the image display apparatus 103, and the number of pixels included in the display screen.

The display-image-data obtaining unit 306 of this embodiment obtains image data used for display from the storing/holding unit 302 in accordance with a control instruction issued by the pixel magnification setting unit 305.

The display data generation unit 307 of this embodiment generates display data to be displayed in the image display apparatus 103 by a magnification change process from the image data obtained by the display-image-data obtaining unit 306 in accordance with a display mode and a pixel magnification set by a pixel magnification setting unit 305. The generation of display data will be described with reference to a flowchart of FIG. 6 hereinafter.

The display-image-data output unit 308 of this embodiment outputs the display data generated by the display data generation unit 307 to the image display apparatus 103 which is an external apparatus.

Hardware Configuration of Image Processing Apparatus

Figure 4:
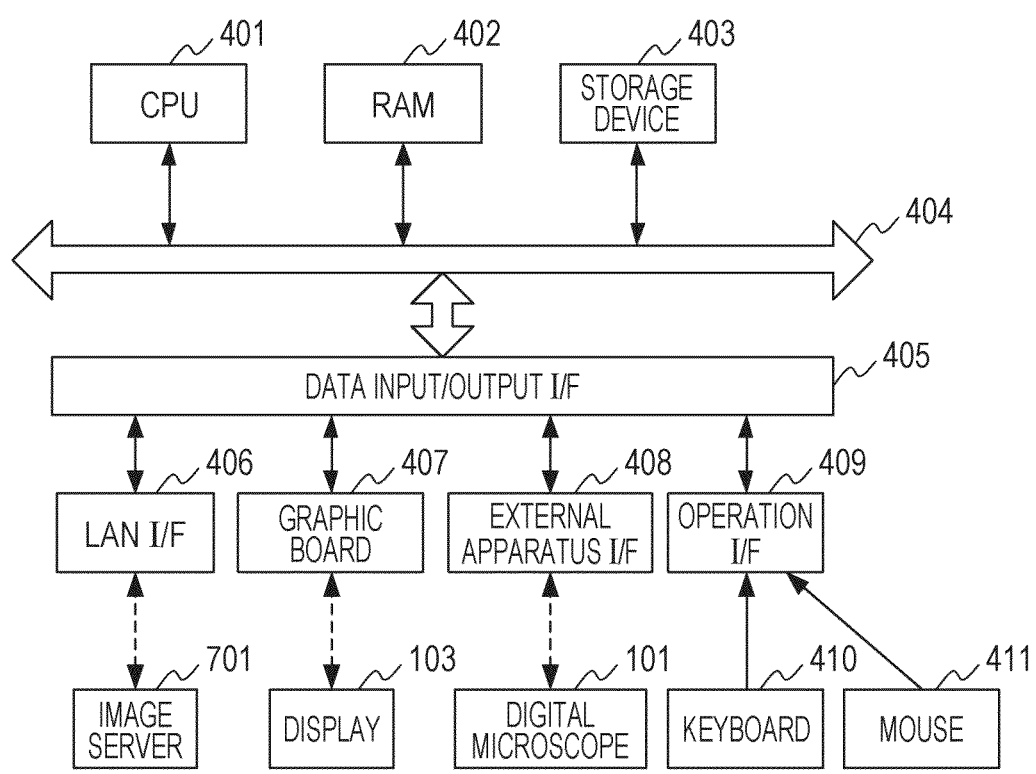
FIG. 4 is a block diagram illustrating a hardware configuration of the image processing apparatus according to the present invention.

FIG. 4 is a block diagram illustrating a hardware configuration of the image processing apparatus according to the present invention. Examples of an apparatus which performs information processing include a PC (Personal Computer).

A PC of this embodiment includes a CPU (Central Processing Unit) 401, a RAM (Random Access Memory) 402, a storage device 403, a data input/output I/F 405, and an internal bus 404 which connects the other units with one another.

The CPU 401 of this embodiment accesses the RAM 402 and the like where appropriate and integrally controls entire blocks of the PC while performing various calculation processes. The RAM 402 is used as a work space of the CPU 401 and temporarily stores an OS, various programs being executed, various data (including the plurality of view field information items of the microscope) to be processed in processes including a process of generating data for display at a time of reproduction of the microscope observation view field which is characterized by the present invention, and the like. The storage device 403 of this embodiment is an auxiliary storage device which records and reads information which firmly stores firmware such as an OS, programs, and various parameters to be executed by the CPU 401. Examples of the storage device 403 include a magnetic disk drive such as an HDD (Hard Disk Drive) or an SSD (Solid State Disk) and a semiconductor device using a flash memory. The storage device 403 of this embodiment stores some of or all of the OS, various programs currently executed, and various data (including the plurality of view field information items of the microscope) to be processed by processes including a process of generating data for displaying a reproduced microscope observation view field characterized by the present invention.

To the data input/output I/F 405 of this embodiment, an image server 701 is connected through a LAN I/F 406, the image display apparatus 103 is connected through a graphic board 407, the image-pickup apparatus 101 such as a virtual slide apparatus or a digital microscope is connected through an external apparatus I/F 408, and a keyboard 410 and a mouse 411 are connected through an operation I/F 409.

The image display apparatus 103 of this embodiment is a display device using liquid crystal, EL (Electro-Luminescence), a CRT (Cathode Ray Tube), or the like. The image display apparatus 103 may be an external apparatus externally connected or may be a PC integrated with an image display apparatus, such as a notebook PC.

As a device to be connected to the operation I/F 409 of this embodiment, a pointing device such as the keyboard 410 or the mouse 411 is expected. However, a screen of the image display apparatus 103 such as a touch panel may be directly used as an input device. In this case, the touch panel may be integrally configured with the image display apparatus 103.

Concept Diagram of Change of Display Magnification

FIGS. 5A to 5E are concept diagrams briefly illustrating a microscope view field and display forms reproduced in a display of the image display apparatus 103.

Figure 5A:
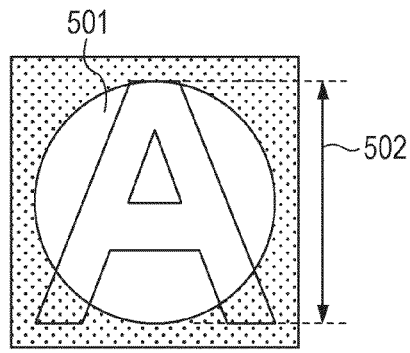
FIGS. 5A to 5E are diagrams schematically illustrating concept of display magnifications.

FIG. 5A is a diagram illustrating a view field obtained when observation is performed using a microscope. The microscope view field is uniquely set in accordance with a magnification of an objective lens and a field number of the microscope. Specifically, the microscope view field is obtained by the following equation:

Actual Field of View of Microscope F.O.V=(Field Number of Objective Lens)/(Magnification of Objective Lens).

Note that, in a case where an actual-view-field microscope is used, the actual field of view of the microscope is obtained by the following equation:

F.O.V=(Field Number of Objective Lens)/((Magnification of Objective Lens)×(Zoom Scale)).

When the microscope is used, an enlarged image of the specimen to be observed is obtained in a circle region 501 as illustrated. Since a region outside the observed region is not illuminated, an image in the region is not recognized. Before virtual slide apparatuses are developed, users, that is, pathologists made diagnoses while viewing such observation images.

A reference numeral 502 denotes a diameter of a microscope observation view field of a circle shape. In practice, the diameter is represented by the number of pixels obtained by dividing the diameter by a pixel pitch of the image-pickup sensor 208. Here, description below is made assuming that a height of a letter "A" is equal to the diameter of the microscope view field.

Figure 5B:
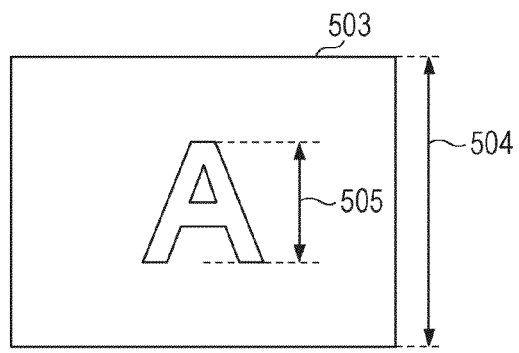

FIG. 5B is a diagram illustrating the display screen at a time of pixel actual-size display. The term "pixel actual-size" represents a state in which pixels obtained by sampling the microscope observation view field as digital data are associated with display elements included in the display one-to-one. When the diameter 502 of the microscope view field is obtained by performing sampling by 1000 pixels, for example, 1000 pixels are also used on a display side. A reference numeral 503 denotes a large display screen of 4k×2k of the image display apparatus 103. A reference numeral 504 denotes a display screen size of the display screen 503 in a vertical direction. Note that a display having an aspect ratio of a small vertical size, that is, a display in a case where the number of pixels in the vertical direction is smaller than the number of pixels in a horizontal direction, is illustrated. Furthermore, a pixel pitch of the display in the vertical direction is the same as that in the horizontal direction. A reference numeral 505 denotes an image display size in the case of the pixel actual-size display. When the diameter 502 of the microscope view field includes 1000 pixels, the image display size 505 also includes 1000 pixels. By this, in the pixel actual-size display, since image data which is an obtainment source is displayed in the pixel actual size, when a size of the display screen 503 is large, image data having an area which is larger than the microscope observation view field may be displayed in the screen.

Figure 5C:
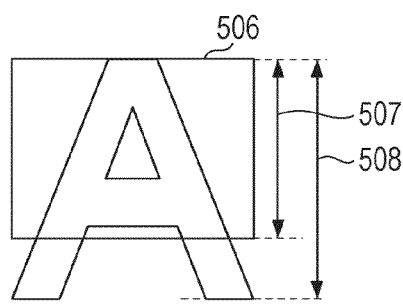

FIG. 5C is a diagram also illustrating a display screen at a time of the pixel actual-size display. Here, a case where an image is displayed in a display which is smaller and which has a lower resolution than those of the display illustrated in FIG. 5B will be described.

A reference numeral 506 denotes a display screen of a comparatively-small image display apparatus which has pixels of 1024×768.

A reference numeral 507 denotes a display screen size in the vertical direction of the display screen 506. Here, the display screen size 507 includes display pixels of 768.

A reference numeral 508 denotes an image size in a case of the pixel actual-size display. Since the display screen size 507 (768 pixels) in the vertical direction is smaller than the number of pixels (1000 pixels) obtained by performing sampling on the microscope observation view field, the entire microscope view field is not displayed. As described above, in the pixel actual-size display, when the size of the display screen 506 is small, only image data included in a range smaller than the microscope observation view field may be displayed in the screen. Note that, as described above, according to the present invention and this specification, a pixel magnification of the pixel actual-size display is defined as 1.

Figure 5D:
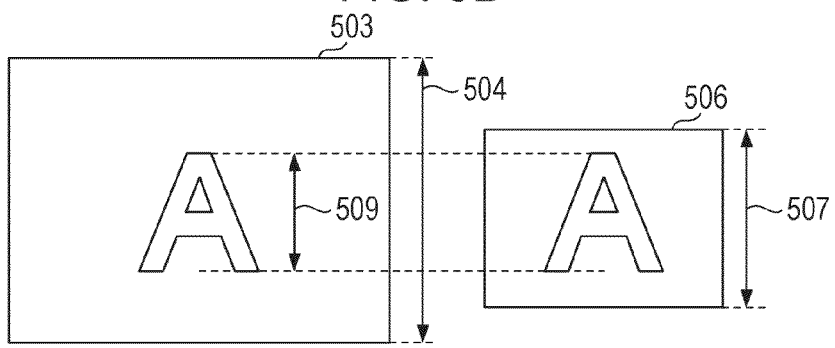

FIG. 5D is a diagram illustrating a display screen in same-size display in which a display magnification is changed so that an image to be processed is displayed in the same size in both of displays having different sizes and different display resolutions. Even in the case of the two different display screens having different sizes illustrated in FIGS. 5B and 5C, sizes of images (physical sizes) displayed in the displays are the same as each other as denoted by a size 509. Note that, as described above, according to the present invention and this specification, a pixel magnification of the same-size display is defined by Equation (1) below.

Pixel Magnification=(Enlargement Magnification)× (Pixel Pitch of Image-Pickup Sensor)/(Pixel Pitch of Display Screen in Image Display Apparatus) (1)

The same-size display is effective in a case of remote diagnosis, such as a case where an object is displayed in the same size in different places or by different users.

Figure 5E:
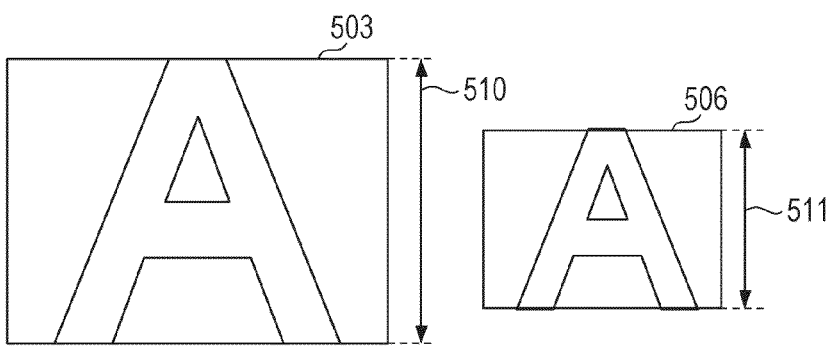

FIG. 5E is a diagram illustrating display screens in a case where the microscope observation view field characterized by the present invention which coincides with display regions of image display apparatuses in terms of a size of view is reproduced. Even when two display screens of different sizes exist similarly to the case of FIG. 5D, when the diameter 502 of the microscope view field coincides with vertical sizes 510 and 511 of the display regions, an image corresponding to the microscope observation field which is familiar for the user may be displayed irrespective of the specification and performance of displays.

Note that a pixel magnification for reproducing the microscope observation view field may be obtained by the following equation.

Pixel Magnification=((the Number of Pixels of Long Side or Short Side of Display Screen of Image Display Apparatus)/((Predetermined Field Number of Microscope)/(Pixel Pitch of Image-Pickup Sensor)))×((Display Magnification in Image Display Apparatus)/(Magnification of Objective Lens in Image Capturing))  (2)

As described above, in a display screen in which the number of pixels in a vertical direction is smaller than the number of pixels in a horizontal direction, the number of pixels in the vertical direction of the display screen corresponds to the number of pixels of a short size included in Equation (2). When the following equation is calculated instead of Equation (2), image data of the entire microscope view field to be displayed in a display screen is generated.

Pixel Magnification=((the Number of Pixels in Vertical Direction of Display Screen of Image Display Apparatus)/((Predetermined Field Number of Microscope)/(Pixel Pitch of Image-Pickup Sensor)))×((Display Magnification in Image Display Apparatus)/(Magnification of Objective Lens in Image Capturing))

As described above, when the entire microscope view field is to be displayed in the display screen, the number of pixels in a short side is assigned to Equation (2).

Note that Equation (2) includes the following case. Specifically, when a number of the pixels are to be used to display information other than information on image display, when a number of the pixels are used as a frame, or when a number of the pixels are used to display another image, "the number of pixels of long side or short side of display screen of image display apparatus" is counted except for the pixels. Furthermore, in Equation (2), an error within 10 pixels is acceptable when the number of pixels of a long side or a short side of the display screen of the image display apparatus is set as a reference.

Display Magnification Changing Process

A flow of a display magnification changing process performed by the image processing apparatus 102 according to the present invention will be described with reference to a flowchart of FIG. 6.

In step S601, information on a size (the number of pixels serving as a screen resolution) of a display area of the display which is the image display apparatus 103 is obtained by the display-device-information obtaining unit 304 from the image display apparatus 103. The information on the size of the display area is used to determine a size of display data to be generated.

In step S602, information on a display magnification of an image currently displayed in the image display apparatus 103 is obtained by the display-device-information obtaining unit 304. In an initial stage, a predetermined magnification is set. The display magnification is used to select image data from among layered images. Furthermore, the display magnification is used to determine a size of display data to be generated. A numeric value of a field number to be used in a mode for reproducing the microscope observation view field described below is also obtained as a predetermined value or obtained in accordance with a user's instruction.

In step S603, display mode setting information is obtained. Here, the display mode includes a mode for reproducing a microscope observation view field and a mode for pixel actual-size display.

In step S604, it is determined whether the user has selected the mode for reproducing a microscope observation view field. When the mode for reproducing a microscope observation view field has been selected, the process proceeds to step S605 whereas when the mode for pixel actual-size display which corresponds to a normal observation view field is selected, the process proceeds to step S607.

In step S605, image data to be displayed in the image display apparatus 103 is obtained from the storing/holding unit 302 in accordance with the information on the size of the display area obtained in step S601 and the display magnification and the information on a field number obtained in step S602.

When the display mode for reproducing a microscope observation view field is selected, image data for displaying a reproduced microscope observation view field is generated in step S606. Specifically, a magnification changing process is performed on the obtained image data in accordance with the calculation equation of a pixel magnification illustrated by Equation (2).

In step S607, image data to be displayed in the image display apparatus 103 is obtained from the storing/holding unit 302 in accordance with the information on the size of the display area obtained in step S601 and the information on the display magnification obtained in step S602.

When the mode for pixel actual-size display which corresponds to the normal observation view field is selected, image data for displaying the normal observation view field is generated in step S608. In this case, a resolution conversion process is performed so that image data of a display magnification similar to that of a layered image obtained in step S602 has a predetermined resolution. A correction process suitable for the characteristics of the image display apparatus 103 is performed where appropriate.

In step S609, the display data generated in step S606 or step S608 is output to the image display apparatus 103.

In step S610, the image display apparatus 103 displays the input display data in the screen.

In step S611, it is determined whether image display is terminated. When the user selects another specimen image or when an operation of a display application is completed, the process is terminated. When the display screen is to be further updated, the process returns to step S602 and the process from step S602 is performed again.

Effect of Embodiment

Since a virtual slide image which is equivalent to an observation field of an optical microscope image is generated, familiar environment of microscope observation may be also reproduced in a display.

Second Embodiment

An image processing system according to a second embodiment of the present invention will be described with reference to the accompanying drawings.

In the first embodiment, a virtual slide image may be displayed as general pixel actual-size display and may be displayed by changing a magnification so that a microscope observation view field is reproduced. In the second embodiment, a function of display in a changed magnification for performing same-size display is added to the first embodiment. Furthermore, in order to more accurately reproduce environment of microscope observation, a circle view-field region is provided so that observation is more easily performed. In the second embodiment, the configurations described in the first embodiment may be employed in configurations other than configurations different from the first embodiment.

Configuration of Apparatuses Included in Image Processing System

Figure 7:
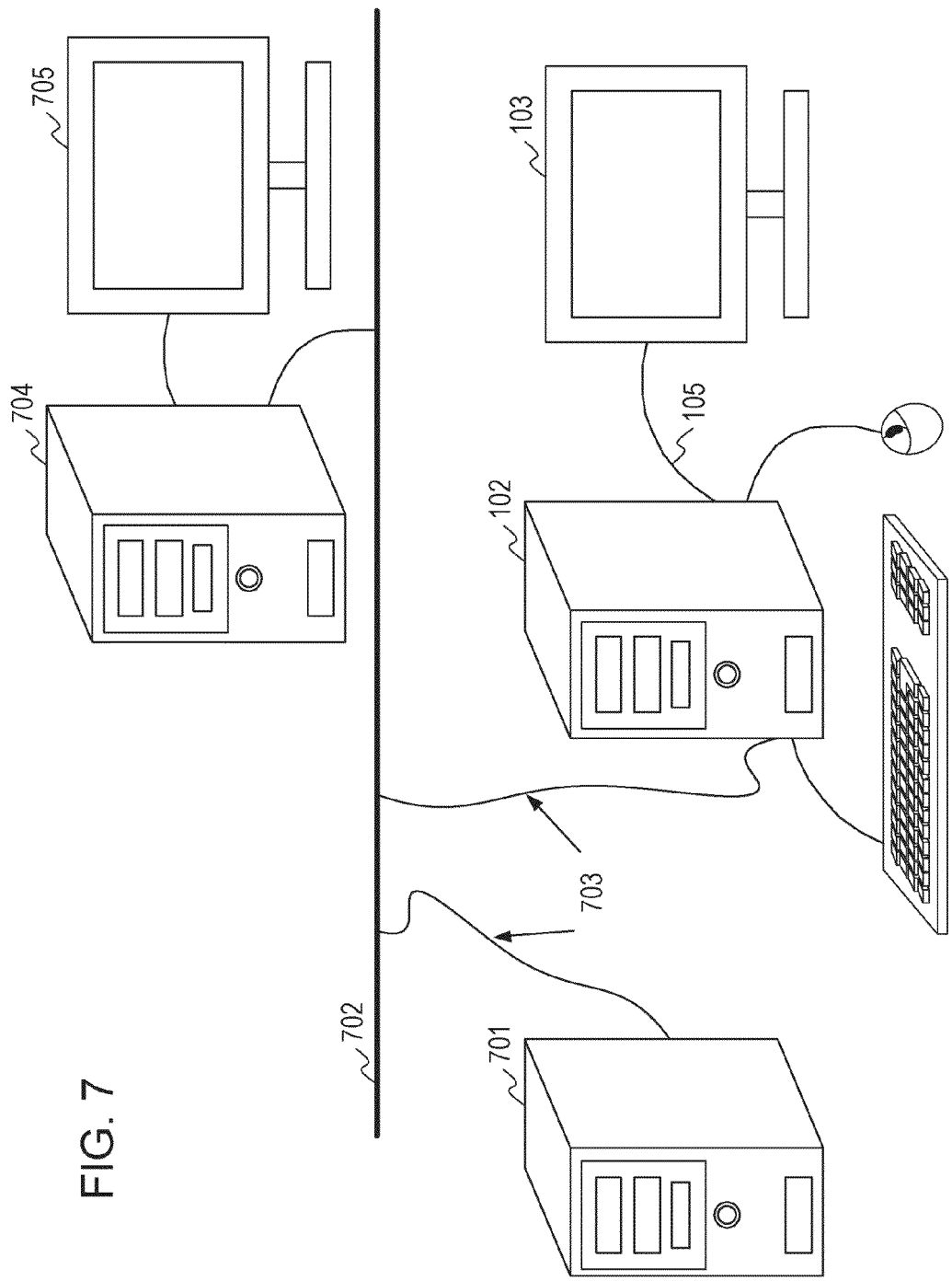
FIG. 7 is an overall view of a configuration of apparatuses included in an image processing system employing an image processing apparatus according to a second embodiment of the present invention.

FIG. 7 is an overall view schematically illustrating a configuration of apparatuses included in an image processing system according to the second embodiment of the present invention.

The image processing system of FIG. 7 employing an image processing apparatus includes an image server 701, an image processing apparatus 102, and an image display apparatus 103, and further includes an image processing apparatus 704 and an image display apparatus 705 connected to the image processing apparatus 704 which are remotely connected through a network 702. The image processing apparatus 102 may obtain image data obtained by capturing an image of a specimen from the image server 701 and generate image data to be displayed in the image display apparatus 103. In this embodiment, the image server 701 and the image processing apparatus 102 are connected by a general-purpose I/F LAN cable 703 through the network 702. The image server 701 of this embodiment is a computer including a mass-storage device which stores image data corresponding to images captured by an image-pickup apparatus 101 which is a virtual slide apparatus. The image server 701 of this embodiment may store layered image data items of different display magnifications as a block in a local storage connected to the image server 701 or may store layered image data items in a distributed manner as entities of the distributed image data items and link information items of the distributed image data items in a server group (a cloud server) provided in a certain location in a network. It is not necessarily the case that the layered image data items are stored in a single server. Note that the image processing apparatus 102 and the image display apparatus 103 are the same as those included in the image processing system of the first embodiment. The image processing apparatus 704 is remotely provided through the network 702. The image processing apparatus 704 functions similarly to the image processing apparatus 102. When obtained image data is stored in the image server 701, both of the image processing apparatuses 102 and 704 may refer to the image data.

In the example of FIG. 7, the image processing system includes five apparatuses, i.e., the image server 701, the image processing apparatuses 102 and 704, and the image display apparatuses 103 and 705. However, a configuration of the present invention is not limited to this configuration. For example, the image processing apparatuses 102 and 704 which are integrated with the image display apparatuses 103 and 705, respectively, may be used, or the image server 701 may have a number of the functions of the image processing apparatuses 102 and 704. Conversely, the functions of the image server 701 and the image processing apparatuses 102 and 704 may be divided and realized by a plurality of apparatuses.

Process of Generating Image Data for Displaying Microscope View Field

Figure 8:
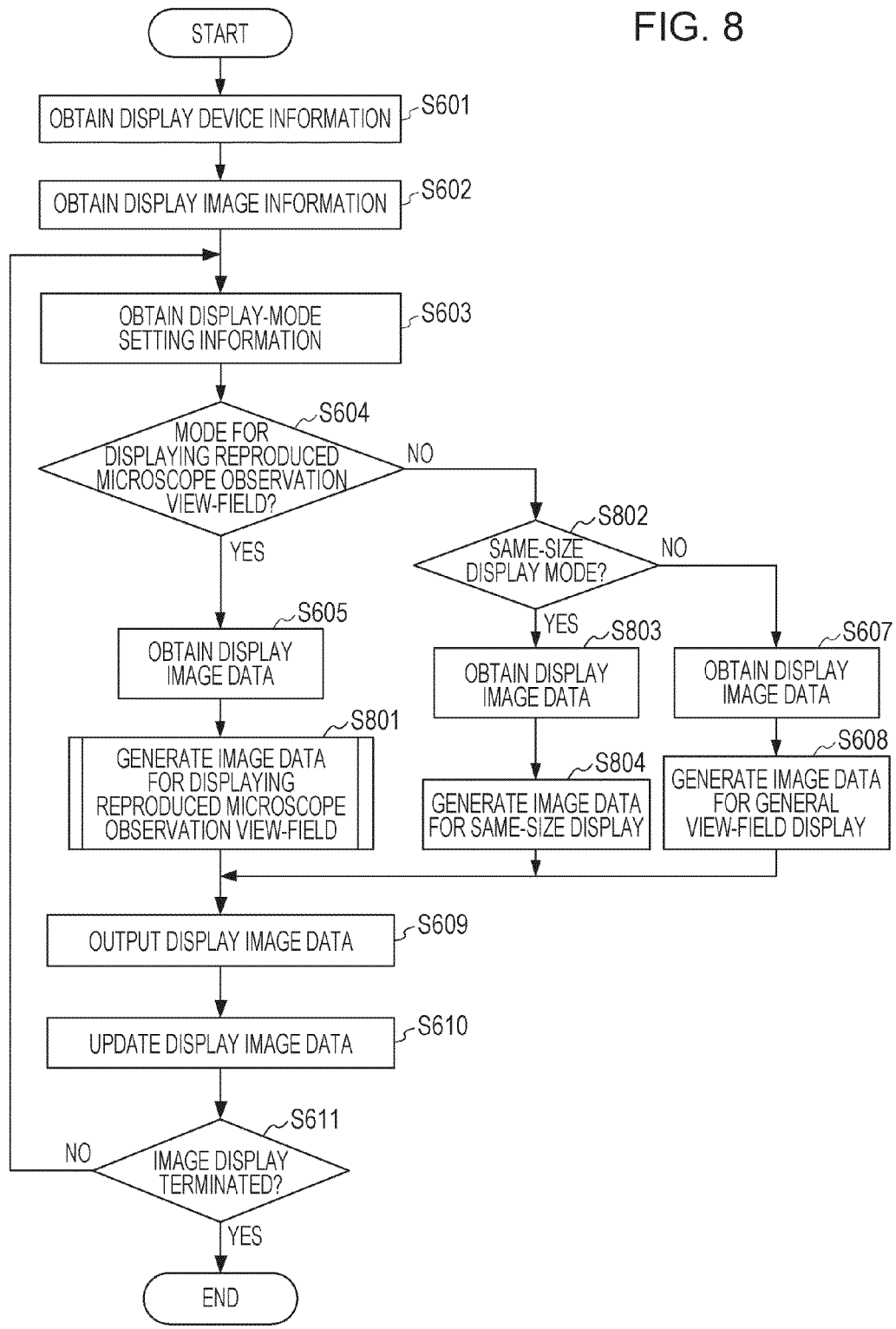
FIG. 8 is a flowchart illustrating a flow of a display magnification changing process performed by the image processing apparatus according to the second embodiment of the present invention.

FIG. 8 is a flowchart illustrating a flow of a process of generating image data for displaying a microscope view field. This process is obtained by adding, to the process of generating image data for displaying a microscope view field according to the first embodiment described with reference to FIG. 6, a magnification changing function for same-size display in which images are displayed in the same size even when specifications including resolutions and performances of the image display apparatuses 103 and 705 are different from each other which is characterized by the present invention. Only a same-size display mode and a process of reproducing a microscope observation view field are different from the process illustrated in FIG. 6, and therefore, only the different portions will be described.

Figure 6:
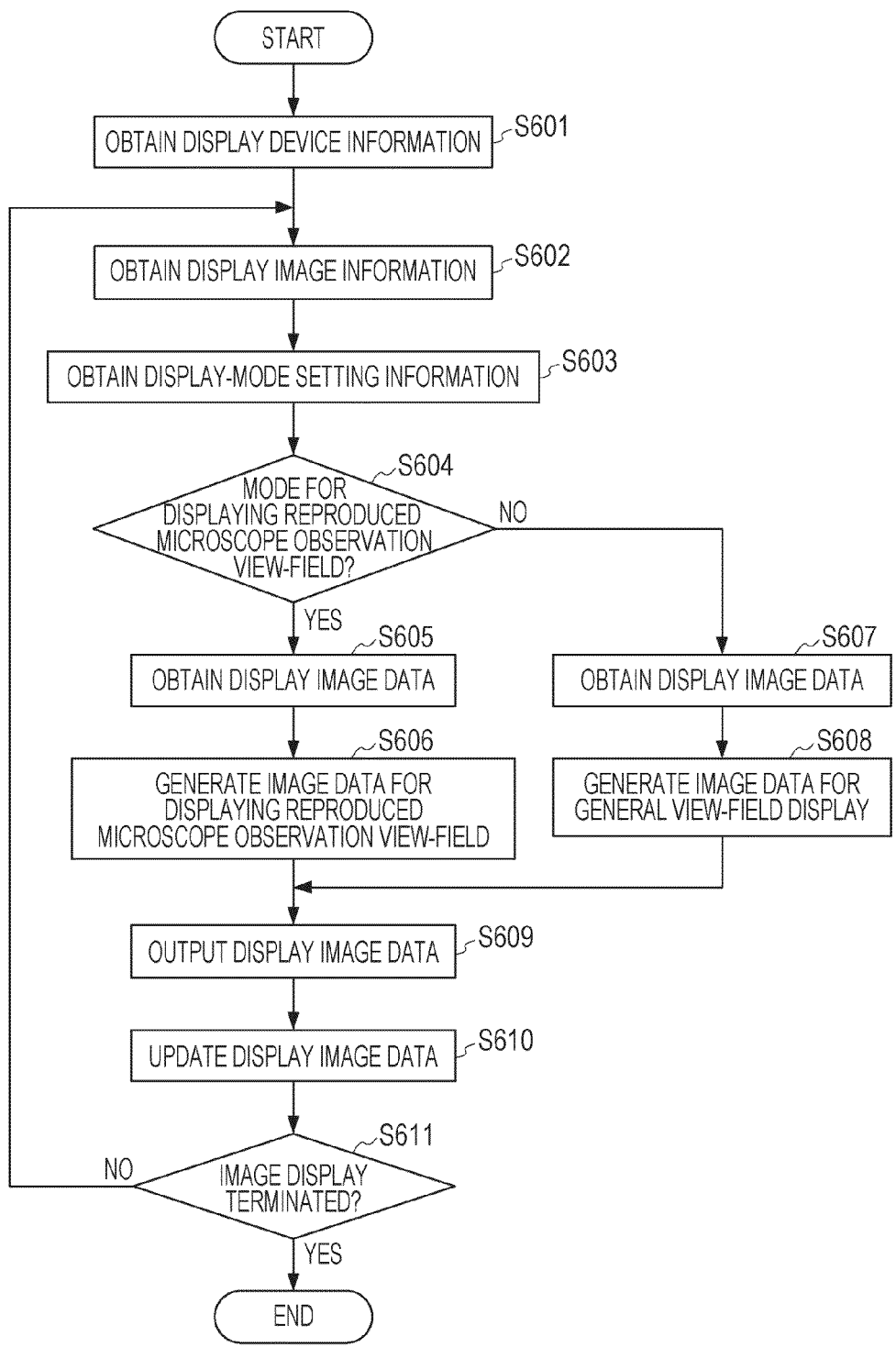
FIG. 6 is a flowchart illustrating a flow of a display magnification changing process performed by the image processing apparatus according to the present invention.

The process of obtaining various information to be used for the magnification changing process caused by change of the pixel magnification and the branching process from step S601 to step S604 have been described in the first embodiment with reference to FIG. 6.

When a display mode for reproducing a microscope observation view field is selected, image data for displaying reproduced microscope observation view field is generated in step S801. Although, as with the operation in step S606, the magnification changing process of a pixel magnification is performed in accordance with Equation (2), a process of displaying a circle region serving as the microscope observation view field is additionally performed. The process will be described in detail with reference to FIG. 9.

When a display mode other than the mode for reproducing the microscope observation view field is selected, it is determined whether same-size display or pixel actual-size display is performed in step S802. When pixel-magnification change for the same-size display is to be performed, the process proceeds to step S803 whereas when a pixel actual-size display mode is selected, the process proceeds to step S607.

In step S803, image data to be displayed in the image display apparatus 103 is obtained from a storing/holding unit 302 in accordance with information on a size of a display area obtained in step S601, information on a size of a display pixel pitch, and a display magnification obtained in step S602.

When the same-size display mode is selected, image data for the same-size display is generated in step S804. Specifically, a magnification changing process is performed on the obtained image data in accordance with a calculation equation of a pixel magnification illustrated by Equation (1).

A process of obtaining display image data in step S605 and a process of obtaining display image data in step S607 to a process in step S611 are the same as those of the first embodiment, and therefore, descriptions thereof are omitted.

Process of Generating Image Data for Displaying Microscope View Field

FIG. 9 is a flowchart illustrating a detailed flow of a process of generating image data for displaying a reproduced microscope observation view field performed in step S801 of FIG. 8.

In step S901, masking information is obtained. The masking information has information items corresponding to display pixels included in a display area of the image display apparatus 103 and includes two types of information including information on a determination as to whether target image data is to be displayed by a luminance value without change or target image data is to be displayed after changing a luminance value which is made for each pixel and information on a determination on a degree of luminance change performed for each display pixel. In a luminance-value shifting process in step S904 onwards, each pixel has a value of five bits, and when the masking information is 0, a value of the image data is used as data for display as it is whereas when the masking information is an arbitrary value, the luminance value is subjected to bit shift in a lower-order direction in accordance with the arbitrary value. For example, in a case of luminance data of 8 bits and 256 gradation levels, when a value of the masking information is 1, bit shift is performed rightward by one bit so that a value of half of the luminance data is obtained. When the luminance data is shifted by 8 bits, a value of the image data is 0, and accordingly, a display pixel is completely masked (a luminance value of a target display pixel is 0). In this embodiment, luminance data of each pixel is a target of calculation with the masking information. However, when RGB color image data is to be processed, the RGB color image data may be temporarily converted into a luminance/color difference signal of a YUV or a YCC and luminance information obtained after the conversion may be subjected to the calculation process. Furthermore, the bit shift may be performed on each of R, G, and B colors. The bit shift may be arbitrarily set to the display pixels included in the display area. However, description will be made hereinafter assuming that a masking value in the circle view field is 0 and a masking value in the other area is 2 in order to reproduce a microscope observation view field. In the region in the display area corresponding to the masking value of 2, a luminance value of obtained image data is reduced to ¼. Furthermore, when meaning is assigned to a specific bit, a process of increasing luminance may be applied.

Furthermore, when a process of changing a luminance value for each display pixel in step S907 onwards is performed, each pixel has a value of 8 bits and a luminance value of a pixel is newly calculated as a result of multiplication of mask information and the luminance value of the image data.

When the mode for displaying a reproduced microscope observation view field is selected, image data for displaying a reproduced microscope observation view field is generated in step S606. Specifically, a magnification changing process is performed on the obtained image data in accordance with a calculation equation of a pixel magnification illustrated by Equation (2). Content of this process is the same as the process described with reference to FIG. 6.

In step 902, it is determined whether a circle display region corresponding to the microscope observation view field is to be set. When the circle display region is to be set, the process proceeds to step S903 whereas when an image is displayed in a screen in a size for reproduction of the microscope view field described in the first embodiment, the process is terminated.

In step S903, it is determined whether a region outside the circle display region is displayed as an image of low luminance after being subjected to a shifting process or displayed as an image of low luminance in a unit of display pixel.

When the shifting process is to be performed, the process proceeds to step S904 whereas when multiplication of masking information and luminance values of pixels is to be performed, the process proceeds to step S907.

When it is determined that the microscope view field is to be reproduced, the values of the masking information obtained and recognized in step S901 are referred to by corresponding pixels in step S904. It is determined whether a value of the masking information of corresponding display pixels which is referred to is 0, that is, whether the pixels have normal luminance displayed as a target region or the pixels have luminance to be lowered out of the microscope observation view field. When the masking value is 0, the process proceeds to step S905 whereas when the masking value is other than 0, that is, when luminance values of the pixels are to be lowered by bit shift, the process proceeds to step S906.

When the masking value is 0, the luminance values of the pixels of the obtained image data are employed as pixel values for display in step S905. Note that, when a correction processing suitable for the characteristics of the image display apparatus 103 is to be performed, the luminance values may be changed.

When the masking value is other than 0, in step S906, the luminance values of the pixels of the obtained image is subjected to bit shift calculation in a lower order direction in accordance with the value of the masking information obtained in step S901. As a result, lowering of luminance in accordance with the masking value is realized.

In step S907, masking information corresponding to each of the pixels of the image data is obtained. The masking information has 8 bits, for example, and is a value from 0 to 255.

In step S908, a luminance value of a pixel and a value of corresponding masking information are subjected to multiplication so that a new luminance value is obtained. In practice, when normalization is performed by dividing a result of the multiplication by 255 which is the maximum value of the masking information, a luminance value the same as that before the division may be obtained in a case where the masking information is 255. Accordingly, also when the same process is performed on each of the pixels, the microscope view field is reproduced. Since the multiplication between the luminance value and the masking information is performed instead of the lowering of luminance by bit shift, a degree of freedom for setting of luminance is further increased. A predetermined value provided in advance may be used as the masking information or the masking information may be changed or newly set in accordance with a user's instruction. Consequently, a shape of the observation view field other than the circle shape representing the microscope view field may be flexibly employed.

Display Screen Layout

Figure 10A:
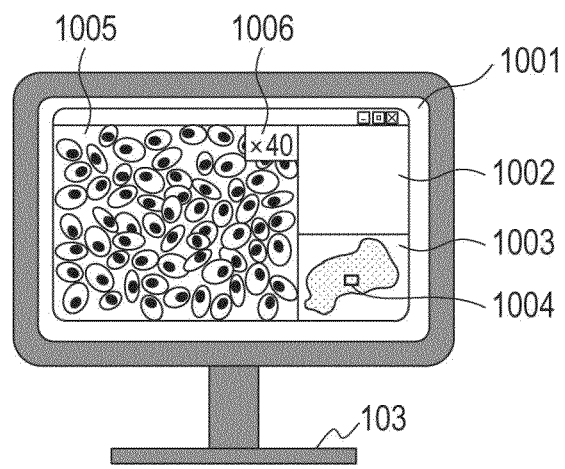
FIGS. 10A to 10C include diagrams illustrating display screens of the image processing system according to the present invention.
Figure 10B:
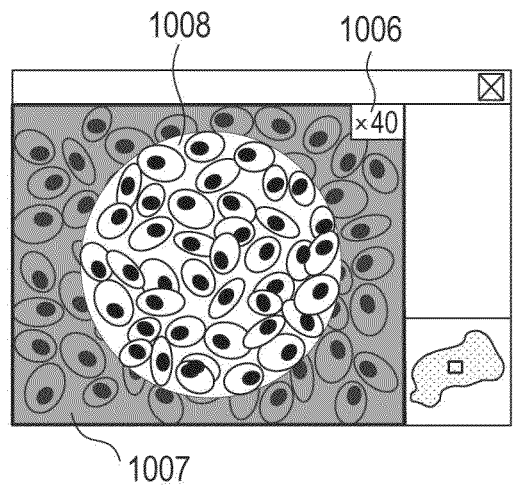
Figure 10C:
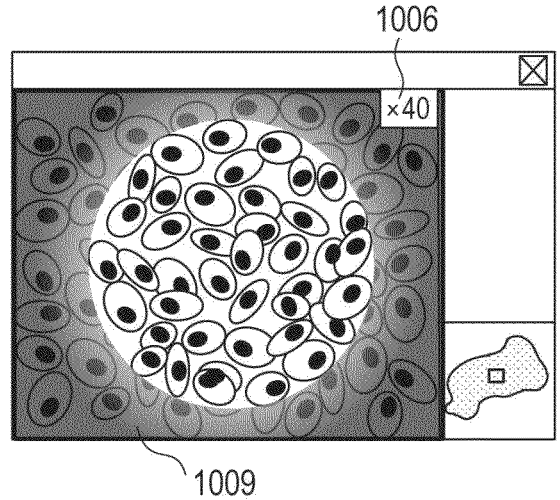

FIGS. 10A to 10C include diagrams illustrating a display screen in a case where display data generated by the image processing apparatus 102 is displayed in the image display apparatus 103. In FIGS. 10A to 10C, two display modes for reproducing the microscope observation view field will be described.

FIG. 10A is a basic configuration of screen layout of the image display apparatus 103. A display screen includes an information area 1002 displaying statuses of display and operations and information on various images, a thumbnail image 1003 of a specimen to be observed, a detail display region 1004 which is included in the thumbnail image 1003 and which displays an area being observed in detail, a display region 1005 displaying image data of the specimen for detailed observation, and a display magnification 1006 of the display region 1005, which are included in a large window 1001. The regions and the images may be displayed by dividing a display region of the large window 1001 for individual functional regions by a single document interface or may be displayed as individual windows by a multiple document interface. The thumbnail image 1003 displays a position and a size of the display region 1005 displaying image data of the specimen in an entire image of the specimen. The position and the size may be recognized by a frame of the detail display region 1004. The detail display region 1004 may be directly set and updated by a user's instruction input to an input device externally connected such as a touch panel or a mouse 411 or may be set and updated by moving the display region in the displayed image or by a scaling operation. The specimen-image-data display region 1005 displays image data of the specimen being observed in detail. Here, an image which is scaled by moving the display region (selection or movement of a partial region to be observed in the entire image of the specimen) or by changing a display magnification in accordance with an operation instruction issued by the user is displayed.

Image data obtained by the virtual slide apparatus is provided as an image obtained by connecting image data items obtained by capturing the specimen in a divided manner. Accordingly, in pixel actual-size display, information may be displayed in a region larger than the microscope view field in the entire screen of the image display apparatus 103. In addition, an action of looking into the microscope is omitted, a view distance is ensured to some extent, and a larger amount of image data and information on the specimen may be simultaneously displayed. Accordingly, usability is improved.

FIG. 10B is a diagram illustrating a display screen obtained when the microscope view field is reproduced and luminance is uniformly lowered in an area outside the microscope observation view field. The reference numeral 1006 denotes a display magnification. It is assumed here that the image is displayed in a high magnification of 40 times an original magnification. A reference numeral 1008 denotes an observation region corresponding to the microscope view field. In the observation region 1008, that is, in the circle view field, an image having normal luminance is displayed. On the other hand, a region 1007 outside the microscope view field has luminance lowered to a certain extent. Although the image of the specimen is displayed in a large display area, the luminance in the region outside the microscope observation view field is lowered so that the microscope observation view field which is familiar in the field of pathology is reproduced while display of a larger amount of image information in a surrounding region which is advantage of the virtual slide apparatus is attained. As a method for reducing an amount of information other than information in the microscope observation view field, in addition to a method for lowering luminance, a method for reducing color information so that monochrome data is displayed may be employed.

FIG. 10C is a diagram illustrating a display screen obtained when the microscope observation view field is reproduced and luminance in a region outside the microscope observation view field is gradually lowered in accordance with a distance from the center of the microscope view field. Luminance in a region 1009 outside the microscope observation view field is gradually lowered in accordance with a distance from the center of a circle region representing the reproduced microscope view field. Here, the luminance of the region outside the microscope observation view field is lowered in accordance with a distance from the center of the circle to be observed without changing display of the image in the microscope observation view field to be observed. When compared with uniform reduction of the information on the region outside the microscope view field illustrated in FIG. 10B, this configuration is convenient since a concerned region is easily found since an amount of information in the region to be observed is increased.

Effects of Embodiment

According to the present invention, an image processing apparatus capable of generating a virtual slide image equivalent to an image of an observation view field viewed using an optical microscope may be provided. In particular, even under environment in which an image display apparatus remotely provided has a different specification, an image may be displayed in the same size. Furthermore, since a circle masking image is used, display by a microscope may be reproduced.

Other Embodiments

The objects of the present invention may be attained as follows. Specifically, a recording medium (or a storage medium) which records program codes of software which realize all of or some of the functions in the foregoing embodiments is supplied to a system or an apparatus. Then a computer (or a CPU or an MPU) included in the system or the apparatus reads and executes the program codes stored in the recording medium. In this case, the program codes read from the recording medium themselves realize the functions of the foregoing embodiments and the recording medium which records the program codes is included in the present invention.

Furthermore, the computer executes the read program codes, and in accordance with instructions of the program codes, an operating system (OS) or the like which operates in the computer performs all actual processes or some of the actual processes. A case where the functions of the foregoing embodiments are realized by the processes may be also included in the present invention.

Furthermore, it is assumed that the program codes read from the recording medium are written in a memory included in a function expansion card inserted into the computer or a function expansion unit connected to the computer. Then a case where, in accordance with instructions of the program codes, a CPU or the like included in the function expansion card or the function expansion unit performs all of or some of the actual processes so that the functions of the foregoing embodiments are realized by the processes may be also included in the present invention.

When the present invention is applied to the recording medium described above, the recording medium stores program codes corresponding to the flowcharts described above.

Furthermore, the configurations according to the first and second embodiments may be combined with each other. For example, under environment in which an image processing apparatus and an image-pickup apparatus are locally connected to each other, one of the three display modes including the same-size display mode described in the second embodiment may be selected. Furthermore, an image processing apparatus may be connected to an image-pickup apparatus and an image server so as to obtain an image to be processed from any of the apparatuses. Moreover, configurations obtained by combining the various techniques according to the foregoing embodiments with one another where appropriate are also included in the present invention. The technical scope of the present invention is defined by claims within a range of the patent claims, and is not limited to the foregoing embodiments.

According to preferred embodiments of the present invention, an image processing apparatus capable of generating a virtual slide image which is equivalent to an image of an observation view field of an optical microscope may be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus which processes virtual slide image data to be displayed in an image display apparatus, the image processing apparatus comprising:
    an image data obtaining unit configured to obtain image data obtained by capturing an image of a target object; and
    an image data generation unit configured to generate display image data corresponding to the image of the target object to be displayed in the image display apparatus in a display magnification corresponding to a predetermined field number of a microscope.

2. The image processing apparatus according to claim 1, wherein the image data generation unit determines the display magnification such that a diameter of a predetermined actual view field of the microscope coincides with a length of a long side or a short side of a display screen of the image display apparatus.

3. The image processing apparatus according to claim 1, wherein the image data generation unit determines the display magnification in accordance with information on a view field of an existing microscope.

4. The image processing apparatus according to claim 1, wherein the image data generation unit determines the display magnification using a predetermined one of a plurality of information items on a view field of an existing microscope as initial information.

5. The image processing apparatus according to claim 1, wherein the image data generation unit determines the display magnification using one of a plurality of information items on a view field of an existing microscope selected by a user.

6. The image processing apparatus according to claim 1, wherein the image data generation unit generates the display image data in accordance with the number of pixels included in the image display apparatus.

7. The image processing apparatus according to claim 1, wherein the image data generation unit generates the display image data in accordance with a magnification of an objective lens at a time when the target image is captured.

8. The image processing apparatus according to claim 1, wherein the image data generation unit generates the display image data of the display magnification corresponding to a pixel magnification represented by the following equation:

Pixel Magnification =((the Number of Pixels of Long Side or Short Side of Display Screen of Image Display Apparatus)/((Predetermined Field Number of Microscope)/(Pixel Pitch of Image-Pickup Sensor)))×((Display Magnification in Display Screen of Image Display Apparatus)/(Magnification of Objective Lens in Image Capturing)).

9. The image processing apparatus according to claim 1, wherein the image data generation unit generates the display image data of the display magnification corresponding to a pixel magnification represented by the following equation:

Pixel Magnification =(Enlargement Magnification)×(Pixel Pitch of Image-Pickup Sensor)/(Pixel Pitch in Display Screen of Image Display Apparatus), wherein the enlargement magnification is obtained by the following calculation:

(Display Magnification)×(Pixel Pitch in Display Screen of Image Display Apparatus)/((Pixel Pitch of Image-Pickup Sensor) x (Magnification of Objective Lens in Image Capturing)).

10. The image processing apparatus according to claim 1, further comprising:
a mode selection unit configured to select at least one of the following three modes (1) to (3) for selecting an image to be displayed in the image display apparatus:
(1) a mode for displaying display image data generated in a pixel magnification represented by the following equation:

Pixel Magnification =((the Number of Pixels of Long Side or Short Side of Display Screen of Image Display Apparatus)/((Predetermined Field Number of Microscope)/(Pixel Pitch of Image-Pickup Sensor)))×((Display Magnification in Display Screen of Image Display Apparatus)/(Magnification of Objective Lens in Image Capturing)), (2) a mode for displaying display image data as pixel actual-size display, and (3) a mode for displaying display image data generated in a pixel magnification represented by the following equation:

Pixel Magnification =(Enlargement Magnification)×(Pixel Pitch of Image-Pickup Sensor)/(Pixel Pitch in Display Screen of Image Display Apparatus), wherein the enlargement magnification is obtained by the following calculation:

(Display Magnification)×(Pixel Pitch in Display Screen of Image Display Apparatus)/((Pixel Pitch of Image-Pickup Sensor)×(Magnification of Objective Lens in Image Capturing)).

11. An image processing method for processing a virtual slide image, comprising:
an image data obtaining step of obtaining image data obtained by capturing an image of a target object; and
an image data generation step of generating display image data representing an image to be displayed in the image display apparatus in a display magnification corresponding to a predetermined field number of a microscope.

12. The image processing method according to claim 11, wherein, in the image data generation step, the display magnification is determined such that a diameter of a predetermined actual view field of the microscope coincides with a length of a long side or a short side of a display screen of the image display apparatus.

13. The image processing method according to claim 11, wherein, in the image data generation step, the display magnification is determined in accordance with information on a view field of an existing microscope.

14. The image processing method according to claim 11, wherein, in the image data generation step, the display magnification is determined using a predetermined one of a plurality of information items on a view field of an existing microscope as initial information.

15. The image processing method according to claim 11, wherein, in the image data generation step, the display magnification is determined using one of a plurality of information items on a view field of an existing microscope selected by a user.

16. The image processing method according to claim 11, wherein, in the image data generation step, the display image data of the display magnification changed by a pixel magnification represented by the following equation is generated:

Pixel Magnification =((the Number of Pixels of Long Side or Short Side of Display Screen of Image Display Apparatus)/((Predetermined Field Number of Microscope)/(Pixel Pitch of Image-Pickup Sensor)))×((Display Magnification in Display Screen of Image Display Apparatus)/(Magnification of Objective Lens in Image Capturing)).

17. The image processing method according to claim 11, wherein, in the image data generation step, the display image data of the display magnification corresponding to a pixel magnification represented by the following equation is generated:

Pixel Magnification =(Enlargement Magnification)×(Pixel Pitch of Image-Pickup Sensor)/(Pixel Pitch in Display Screen of Image Display Apparatus), wherein the enlargement magnification is obtained by the following calculation:

(Display Magnification)×(Pixel Pitch in Display Screen of Image Display Apparatus)/((Pixel Pitch of Image-Pickup Sensor)×(Magnification of Objective Lens in Image Capturing)).

18. An image processing system comprising:
the image processing apparatus set forth in claim 1; and
an image display apparatus configured to display a virtual slide image processed by the image processing apparatus in a display magnification corresponding to a predetermined field number of a microscope.

19. A non-transitory computer-readable storage medium storing a program which causes a computer to execute the steps of the image processing method set forth in claim 11.

\* \* \* \* \*